(12) United States Patent
Mathew et al.

(10) Patent No.: US 7,579,184 B2
(45) Date of Patent: Aug. 25, 2009

(54) METHODS TO INCREASE DYNAMIC RANGE AND IMPROVE QUANTITATIVE ANALYSIS IN RAPID BIOSENSORS

(75) Inventors: Finny Mathew, East Lansing, MI (US); David Olson, Ann Arbor, MI (US); Zarini Muhammad-Tahir, East Lansing, MI (US); John Cunningham, Dexter, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 327 days.

(21) Appl. No.: 11/443,531

(22) Filed: May 30, 2006

(65) Prior Publication Data

US 2006/0275853 A1 Dec. 7, 2006

Related U.S. Application Data

(60) Provisional application No. 60/686,763, filed on Jun. 2, 2005.

(51) Int. Cl.
*G01N 33/553* (2006.01)

(52) U.S. Cl. .............. 435/287.2; 204/400; 204/403.01; 422/82.01; 435/6; 435/287.1; 435/287.9; 435/288.5; 436/524; 436/525; 436/806

(58) Field of Classification Search .............. None
See application file for complete search history.

(56) References Cited

U.S. PATENT DOCUMENTS

| 5,137,827 A * | 8/1992 | Mroczkowski et al. ... 435/287.2 |
| 6,315,926 B1 | 11/2001 | Jansen |
| 6,331,356 B1 | 12/2001 | Angelopoulos et al. |
| 6,333,145 B1 | 12/2001 | Cloots et al. |
| 6,333,425 B1 | 12/2001 | Michot et al. |
| 2003/0153094 A1 | 8/2003 | Alocilja et al. |

* cited by examiner

*Primary Examiner*—Christopher L Chin
(74) *Attorney, Agent, or Firm*—Ian C. McLeod

(57) ABSTRACT

Conductimetric assay devices that have both low end and high end sensitivity are described. The geometric shape and/or arrangement of the capture zones make it possible for the assay devices to have both low end and high end sensitivity. Also described is a conductimetric assay device having a pre-capture zone to capture unbound analyte. The assay device overcomes the problem of flooding by the analyte.

15 Claims, 8 Drawing Sheets

METHODS TO INCREASE DYNAMIC RANGE AND IMPROVE QUANTITATIVE ANALYSIS IN RAPID BIOSENSORS

CROSS-REFERENCE TO RELATED APPLICATIONS

This application claims benefit of Provisional Application No. 60/686,763, filed Jun. 02, 2005.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to conductimetric assay devices. Specifically, the present invention relates to improved conductimetric assay devices having both high sensitivity and a broad dynamic range.

(2) Description of the Related Art

A key technical challenge for rapid biosensors is obtaining both high sensitivity and a broad dynamic range. Highly sensitive detectors can be overwhelmed by high concentrations of analytes. This problem with dynamic range leads to the risk of false negatives due to overload in a sensor tuned for high sensitivity. The problem also distorts that standard curve of sensor signal to analyte concentration, weakening the sensor's ability to provide quantitative analysis of analyte concentration.

OBJECTS

It is an object of the present invention to provide a more reliable assay. Further, it is an object of the present invention to provide an assay which is economical and relatively easily fabricated.

These and other objects will become increasingly apparent by reference to the following description and drawings.

SUMMARY OF THE INVENTION

In some embodiments of the present invention, a sandwich type assay is provided which uses at least one preliminary stage and preferably multiple stages to remove excess proteins of analyte in a sample to prevent overloading in the later detection stage. In some embodiments, the preliminary stages have surfaces coated with a capture agent which diminishes in surface area as the analyte flows across the surface to reach the detection stage. Thus, the present invention provides an improvement in a sandwich type assay method for detection of an analyte conductimetrically in a flowing fluid containing the analyte wherein a first capture agent is bound to a substrate and a second capture agent with a conductive moiety binds to the analyte to produce a conductive signal between spaced electrodes at a first stage which comprises: flowing the fluid over a third capture agent in at least one preliminary second stage in an attempt to determine a portion of the analyte in the second stage; and independently measuring a concentration of the analyte at each stage between the spaced apart electrodes so as to determine if there is an overload of the analyte in the assay.

In further embodiments, multiple of the electrodes are in a parallel pyramidal configuration and the analyte flows in the fluid from an apex towards a base of the pyramid. In still further embodiments, the analyte is captured in a lateral flow type device. In further still embodiments, the second stage has a larger surface area than the first stage.

The present invention provides a conductimetric assay device for use in a sandwich type assay wherein a first capture agent is bound to a substrate and a second capture agent with a conductive moiety binds the analyte to produce a conductive signal between two spaced electrodes at a first stage, the improvement which comprises: a pre-binding third bound capture agent in at least one second stage so that a concentration of the analyte can be measured at each stage between the spaced apart electrodes so as to determine an overload of the analyte.

In further embodiments, the multiple of the spaced apart electrodes are in a parallel pyramidal configuration so that the fluid flows from an apex to a base of the pyramidal which enables pre-binding of excess of the analyte. In still further embodiments, the assay device is a lateral flow device. In further still embodiments, the second stage has a larger surface area than the first stage.

The present invention provides a conductimetric assay device for the detection of an analyte in a flowing fluid sample comprising: a capture zone having a length along which the fluid sample flows over a substrate and an increasing width; a set of two electrodes spaced across the increasing width of the capture zone linked to a circuit such that a distance between the set of two electrodes increases along the direction of flow of the fluid sample; a first capture agent capable of binding the analyte affixed to the substrate; and a second capture agent with a conductive moiety capable of binding to the analyte in the fluid, while the second capture agent binds to the analyte thereby holding the first capture agent with the conductive moiety between the two electrodes to complete the circuit and produce a conductive signal.

In further embodiments, the conductimetric assay device further comprises a pre-capture zone upstream of the capture zone having a third capture agent capable of binding analyte that is not bound to the second capture agent, such that after the fluid sample mixes with the second capture agent any remaining free analyte is removed from the flowing fluid sample in the pre-capture zone prior to entering the capture zone.

The present invention provides a conductimetric assay device for the detection of an analyte in a flowing fluid sample comprising: a capture zone; a series of two or more separate tracks arranged in series in the capture zone each track having a length along a direction which the fluid sample flows over a substrate and each having a width, each successive track along the direction of flow of the fluid sample having a greater length than a previous capture zone; a set of two electrodes spaced at a distance across the width of each of the separate tracks and linked to an independent circuit; a first capture agent capable of binding the analyte affixed to a substrate on each of the separate tracks; and a second capture agent with a conductive moiety capable of binding to the analyte in the fluid, while the second capture agent binds to the analyte thereby holding the first capture agent with the conductive moiety between the two electrodes to complete the independent circuit and produce a conductive signal.

In further embodiments, the conductimetric assay device further comprises a pre-capture zone upstream of the capture zone having a third capture agent capable of binding analyte that is not bound to the second capture agent, such that after the fluid sample mixes with the second capture agent any remaining free analyte is removed from the flowing fluid sample in the pre-capture zone prior to entering the capture zone. In still further embodiments, the width of each of the two or more separate tracks increases along the direction of flow such that a distance between the set of two electrodes increases along the direction of flow of the fluid sample.

The present invention provides a conductimetric assay device for the detection of an analyte in a flowing fluid sample comprising: a capture zone; two or more separate tracks in the capture zone each track having a length along which a portion of the fluid sample flows over a substrate arranged in a parallel conformation and each having different widths; a set of two electrodes spaced at a distance across the width of each of the separate tracks and linked to an independent circuit such that the distance between the set of two electrodes is different for each track; a first capture agent capable of binding the analyte affixed to a substrate on each of the separate tracks; and a second capture agent with a conductive moiety capable of binding to the analyte in the fluid, while the second capture agent binds to the analyte thereby holding the first capture agent with the conductive moiety between the two electrodes to complete the independent circuit and produce a conductive signal.

In further embodiments, the conductimetric assay device further comprises a pre-capture zone upstream of the capture zone having a third capture agent capable of binding analyte that is not bound to the second capture agent, such that after the fluid sample mixes with the second capture agent any remaining free analyte is removed from the flowing fluid sample in the pre-capture zone prior to entering the capture zone. In still further embodiments, the width of the two or more separate tracks increases along the direction of flow such that a distance between the set of two electrodes increases along the direction of flow of the fluid sample.

The present invention provides an improvement in a conductimetric assay device for the detection of an analyte in a flowing fluid sample containing the analyte wherein a first capture agent is bound to a substrate in a capture zone and a second capture agent with a conductive moiety binds to the analyte and the analyte binds to the first capture agent thereby capturing the conductive moiety in the capture zone between two spaced electrodes to complete a circuit and produce a conductive signal, the improvement which comprises: a pre-capture zone upstream of the capture zone having a third capture agent capable of binding analyte that is not bound to the second capture agent, such that after the fluid sample mixes with the second capture agent any remaining free analyte is removed from the flowing fluid sample in the pre-capture zone prior to entering the capture zone.

The present invention provides a method of determining whether an analyte of interest is present in a fluid sample comprising: providing the conductimetric assay device comprising a capture zone having a length along a direction which the fluid sample flows over a substrate and an increasing width; a set of two electrodes spaced across the increasing width of the capture zone linked to a circuit such that a distance between the set of two electrodes increases along the direction of flow of the fluid sample; a first capture agent capable of binding the analyte affixed to the substrate; and a second capture agent with a conductive moiety capable of binding to the analyte in the fluid, while the second capture agent binds to the analyte thereby holding the first capture agent with the conductive moiety between the two electrodes to complete the circuit and produce a conductive signal; providing the sample to an absorbent sample pad of the device; measuring a change in conductance across the set of two electrodes; and determining whether the analyte of interest is present by the measured change in conductance across the two electrodes.

The present invention provides a method of estimating a concentration of an analyte in a fluid sample comprising: providing a conductimetric assay device comprising a capture zone; a series of two or more separate tracks arranged in series in the capture zone each track having a length along a direction which the fluid sample flows over a substrate and each having a width each successive track along the direction of flow of the fluid sample having a greater length than a previous capture zone; a set of two electrodes spaced at a distance across the width of each of the separate tracks and linked to an independent circuit; a first capture agent capable of binding the analyte affixed to a substrate on each of the separate tracks; and a second capture agent with a conductive moiety capable of binding to the analyte in the fluid, while the second capture agent binds to the analyte thereby holding the first capture agent with the conductive moiety between the two electrodes to complete the independent circuit and produce a conductive signal; providing the sample to an absorbent sample pad of the device; measuring the change in conductance across each set of two electrodes for each of the tracks; determining whether the track registers a positive signal for the analyte of interest by the measured change in conductance across the two electrodes; and counting the number of tracks forming closed circuits as an estimate the concentration of the analyte.

The present invention provides a method of estimating a concentration of an analyte in a fluid sample comprising: providing a conductimetric assay device comprising a capture zone; two or more separate tracks in the capture zone each track having a length along which a portion of the fluid sample flows over a substrate arranged in a parallel conformation and each having different widths; a set of two electrodes spaced at a distance across the width of each of the separate tracks and linked to an independent circuit such that the distance between the set of two electrodes is different for each track; a first capture agent capable of binding the analyte affixed to a substrate on each of the separate tracks; and a second capture agent with a conductive moiety capable of binding to the analyte in the fluid, while the second capture agent binds to the analyte thereby holding the first capture agent with the conductive moiety between the two electrodes to complete the independent circuit and produce a conductive signal; providing the sample to an absorbent sample pad of the device; measuring the change in conductance across each set of two electrodes for each of the tracks; determining whether the track registers a positive signal for the analyte of interest by the measured change in conductance across the two electrodes; and counting the number of tracks forming closed circuits as an estimate the concentration of the analyte.

The present invention provides a method of determining whether an analyte of interest is present in a fluid sample comprising: providing a conductimetric assay device wherein a first capture agent is bound to a substrate in a capture zone and a second capture agent with a conductive moiety binds to the analyte and the analyte binds to the first capture agent thereby capturing the conductive moiety in the capture zone between two spaced electrodes to complete a circuit and produce a conductive signal, the improvement which comprises a pre-capture zone upstream of the capture zone having a third capture agent capable of binding analyte that is not bound to the second capture agent, such that after the fluid sample mixes with the second capture agent any remaining free analyte is removed from the flowing fluid sample in the pre-capture zone prior to entering the capture zone; providing the sample to an absorbent sample pad of the device; measuring a change in conductance across the two electrodes; and determining whether the analyte of interest is present by the measured change in conductance across the two electrodes.

BRIEF DESCRIPTION OF THE DRAWINGS

FIG. 7A illustrates how the device 510 is set up. FIG. 7B illustrates how the device functions during use. The binding antibody ($Y_a$) recognizes a region of the analyte that is different from the region recognized by the capture antibody ($Y_b$).

DETAILED DESCRIPTION OF THE INVENTION

Figure 1:
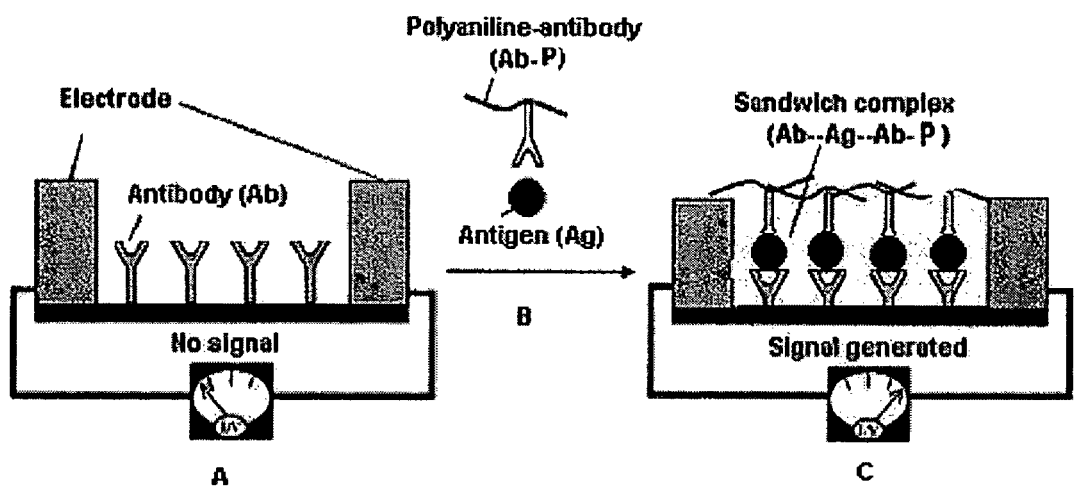
FIG. 1 is a schematic view of a cross-section of the capture zone of a conductimetric assay device before (A) and after (C) antigen capture.

All patents, patent applications, government publications, government regulations, and literature references cited in this specification are hereby incorporated herein by reference in their entirety. In case of conflict, the present description, including definitions, will control.

The term "sandwich assay" as used herein refers to an assay which relies upon more than one capture agent to selectively bind to an analyte. In the present biosensor devices, one of the capture agents is bound to or is a moiety of the substrate and the other is bound to or a moiety of a conductive molecule.

The term "analyte" as used herein refers to any chemical or biological material including, but not limited to proteins, polysaccharides, DNA and living cells in a sample which can detected by means of the biosensor device.

The term "the direction of flow" of the fluid sample as used herein refers to the direction along which the fluid sample moves during the assay procedure.

The term "upstream" as used herein refers to a location along the direction of flow of the fluid sample that is closer to a source of the sample flow than another location. Thus, a first location is upstream of a second location if the fluid sample reaches it during the assay procedure prior to the second location.

The term "zone" means a region of the biosensor where a particular reaction or reactions occur in the biosensor device.

The term "capture zone" as used herein refers to a region of a conductimetric assay device that binds the analyte and thereby captures the second capture agent with the conductive moiety between the electrodes.

The term "track" as used herein refers to a portion of a capture zone that binds the analyte and captures the second capture agent with the conductive moiety between a set of two electrodes connected to an independent circuit.

The term "arranged in series" as used herein refers to a conformation of tracks wherein the tracks are arranged sequentially along the direction of flow of the fluid sample, such that a single fluid sample flows over each zone sequentially.

The term "arranged in parallel" as used herein refers to a conformation of tracks wherein each of the tracks extend along the direction of flow of the fluid sample, such that only a portion of the fluid sample flows over each zones.

The term "length" of the capture zone or track is the dimension of the capture zone along the direction of flow of the fluid sample.

The term "width" of the capture zone or track is the dimension of the capture zone perpendicular to the direction of flow of the fluid sample. In some embodiments, the width of the capture zone or track increases along the direction of flow of the fluid sample from a narrow portion to a wide portion. The width can increase linearly, such that the capture zone or track is triangular in shape. Devices having capture zones or tracks wherein the width does not increase linearly are also encompassed by the present invention, such that the capture zone or track has a convex or concave edge. Such capture zones or tracks can have edges that are parabolic or hyperbolic.

The term "substrate" as used herein refers to a non-conductive material, such as membranes, silicon, paper, plastic or glass, which serves as a support for the biosensor.

The term "capture agent" as used herein refers to any agent that can selectively bind to the analyte. Included within the term "capture agent" are selective antibodies, lectins, DNA, enzymes, proteins and chemicals which bind the analyte in the biosensor device.

The term "free analyte" as used herein refers to analyte that is not bound to the second capture agent.

The term "conductive moiety" as used herein refers to a moiety such as a polymer which is conductive and which is fluid mobile when bound to an analyte, particularly when bound with a capture agent. Included within the term "conductive polymer" are polyanilines, polypyrrole, polythiophenes and which are dispersible in water and are conductive because of the presence of an anion or cation in the polymer. Other electrically conducting polymers include substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof. Illustrative are the conductive polymers described in U.S. Pat. Nos. 6,333,425, 6,333,145, 6,331,356 and 6,315,926 that is capable of conducting electricity, such as polypyrrole.

The term "pre-capture zone" as used herein refers to a zone upstream of the capture zone having a third capture agent that is capable of binding free analyte. Thus, after the fluid sample mixes with the second capture agent any remaining free analyte is removed from the flowing fluid sample in the pre-capture zone prior to entering the capture zone.

The present invention relates to conductimetric biosensors, such as described in U.S. Patent Application Publication No. 2003/0153094, Ser. No. 10/074,499, to Alocilja et al., hereby incorporated herein by reference in its entirety. U.S. Patent Application Publication No. 2003/0153094 to Alocilja et al. and the present application are both assigned to Board of Trustees of Michigan State University. The present invention details several alternate designs that can overcome the limitation of analyte overload and the corresponding problems of reduced dynamic range and ability to deliver quantitative results. The designs here can apply to any assay or sensor that requires a two step binding process: 1) analyte binds to binding agent in solution, 2) analyte-binding agent then binds to a capture agent, typically anchored to a surface; the binding agent-analyte-capture agent complex then triggers a detection signal.

The specific examples given are directed to conductimetric biosensors known in the art of the type as shown in FIG. 1. As shown, the conductimetric biosensor employs a first capture agent bound to a substrate, for example a capture antibody (Ab) that is bound to a plate or other planar surface. The capture antibody (Ab) captures an analyte of interest, such as an antigen (Ag). A second capture agent having a conductive moiety, for example a binding antibody linked to a conductive polymer such as polyaniline (Ab-P) also binds the antigen (Ag). The second capture agent binds to the antigen (Ag) and the analyte binds to the antibody (Ab) to form a complex on the plate between a set of spaced electrodes. The capture of the antigen/antibody/polymer complex creates a conductive bridge between the electrodes, closing a circuit (not shown) to produce a conductive signal. A challenge when using the biosensor arrangement illustrated in FIG. 1 is dealing with the trade off between low end and high end sensitivity, resulting in limited dynamic range. The trade off is affected by sample concentration and the surface area of the capture zone.

Trade offs to get low end sensitivity: Two ways to improve low sensitivity are 1) test larger, more concentrated samples and 2) decrease the surface area and/or width of the capture zone. However, both of these solutions can result in distorted data and possible false negatives: (1) Increasing the amount of sample loaded increases the total amount of analyte available per test. However, this also increases the concentration of non-analyte material in the test, increasing the likelihood of non-specific interactions that can distort the data, increasing the background signal and interfering with specific binding, result in false positives. (2) As the surface area of the capture zone decreases and/or the distance between the electrodes decreases, and the amount of complex needed to complete the circuit decreases, thus low end sensitivity is optimized. But the small surface area can become clogged if the concentration of non-analyte substances is high. Clogging is problematic because non-conductive material can reduce the conductivity of the bound complex, possibly producing an artificially low signal, especially when high concentrations of analytes are present. Also, as the surface area decreases, so does the total amount of capture antibody. Small amounts of capture antibody can become saturated if the concentration of analyte is high, resulting in a poor correlation between signals and increasing amounts of analyte at the upper end of the dynamic range.

Trade offs to get high end sensitivity: Two ways to reduce clogging are 1) test smaller, more dilute samples and 2) increase the surface area of the capture zone. These solutions also have downsides: (1) Decreasing the amount of sample loaded decreases the concentration of non-analyte material in the test, decreasing the likelihood of non-specific interactions that can distort the data and decreasing the background signal. However, this also decreases the total amount of analyte available per test, making it difficult to detect low concentrations of analyte. (2) A large surface area and/or wide channel are less likely to become clogged. Also, the amount of capture antibody present increases with surface area, which allows for more complex to bind, which allows for binding of large amounts of complex before saturation occurs—this increases the upper end of the dynamic range. However, as the surface area of the capture zone increases, the amount of complex needed to complete the circuit increases, this low end sensitivity is lost.

None of the trade offs listed above can simultaneously achieve low end sensitivity and broad dynamic range. Also, none of these scenarios are inherently quantitative.

Geometric Solutions: The designs of the five embodiments schematically illustrated in FIG. 2-6 show how a single sensor can have both low end and high end sensitivity. The key lies in the shape and/or arrangement of the planar capture zone.

Figure 2:
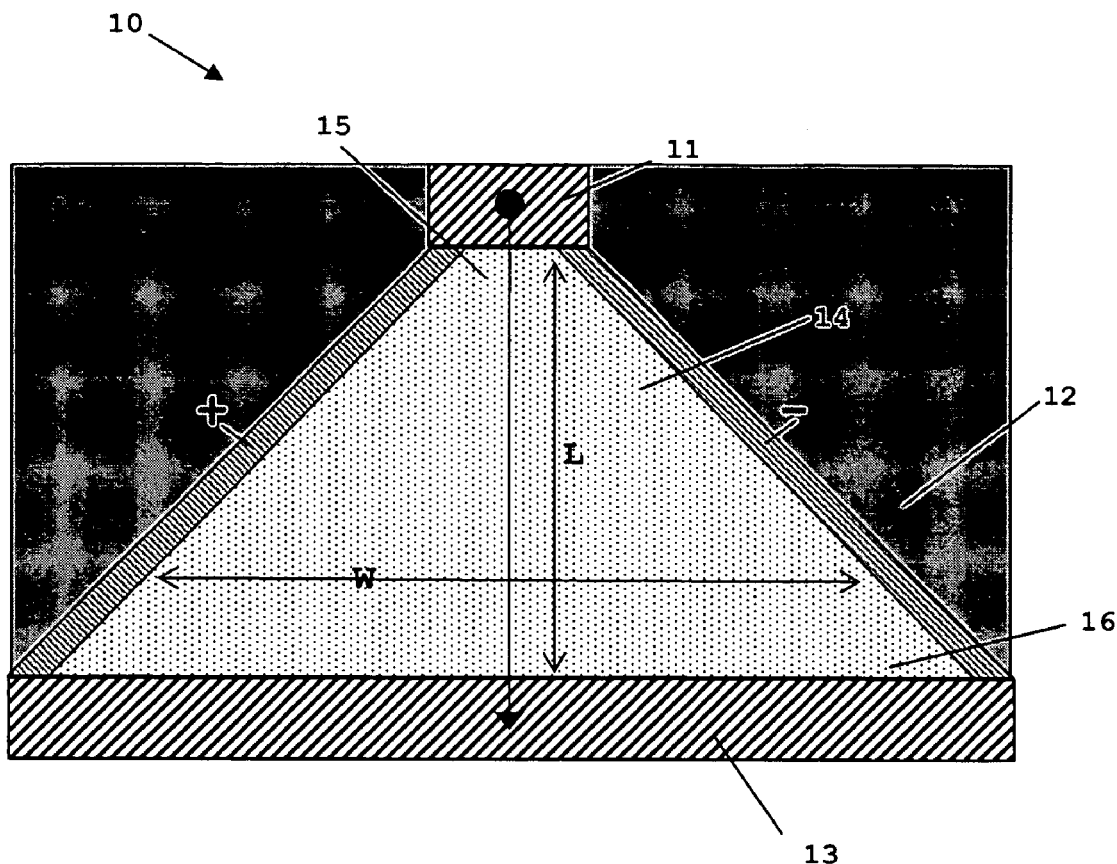
FIG. 2 is a schematic illustration of a first embodiment of a device 10 of the present invention.

First Geometric Embodiment: FIG. 2 schematically illustrates a first embodiment of a conductimetric assay device 10 of the present invention. In this embodiment, a capture zone 14 over a plate 12 has a length L parallel to the direction of flow (arrow) and an increasing width W from a narrow portion 15 at an apex to a wide portion 16 at a base of the triangular capture zone 14. The sample flows from an origin in a sample pad 11 at the narrow portion 15 and flows across the capture zone 14 to a second absorbent pad 13. A set of two electrodes (+,−), one anode (−) and one cathode (+), are spaced across the increasing width (W) of the capture zone 14 and linked to a circuit (not shown). Thus, the distance between the two electrodes (+,−) increases along the direction of flow (arrow) of the fluid sample. A first capture agent capable of binding the analyte such as a specific antibody is affixed to the substrate to form an antibody coated section as the capture zone 14. A second capture agent with a conductive moiety, capable of binding to the analyte, is mixed in the flowing fluid sample. The second capture agent binds to the analyte and this complex is then bound by the first capture agent in the capture zone 14. The conductive moiety is thereby captured between the two electrodes (+,−). The presence of the conductive moiety, which reflects the presence of the analyte, completes the circuit (not shown) and increased the conductance of the circuit so as to produce a conductive signal to detect the analyte.

In this embodiment of the device 10, the width W of the capture zone 14 begins narrow at the narrow portion 15 and becomes progressively wider at the wide portion 16, as measured perpendicularly to the direction of flow (arrow) of the analyte in the fluid sample when the device 10 is used. Low concentrations of the complex of the analyte and the second capture agent with the conductive moiety will saturate the narrow portion 15 of the width W of the capture zone 14, completing the circuit and yielding low-end sensitivity. High concentrations of the complex are absorbed by the increasing surface area of the capture zone 14 as a result of the increasing width W. The arrangement of the device 10 is not inherently quantitative.

Figure 3:
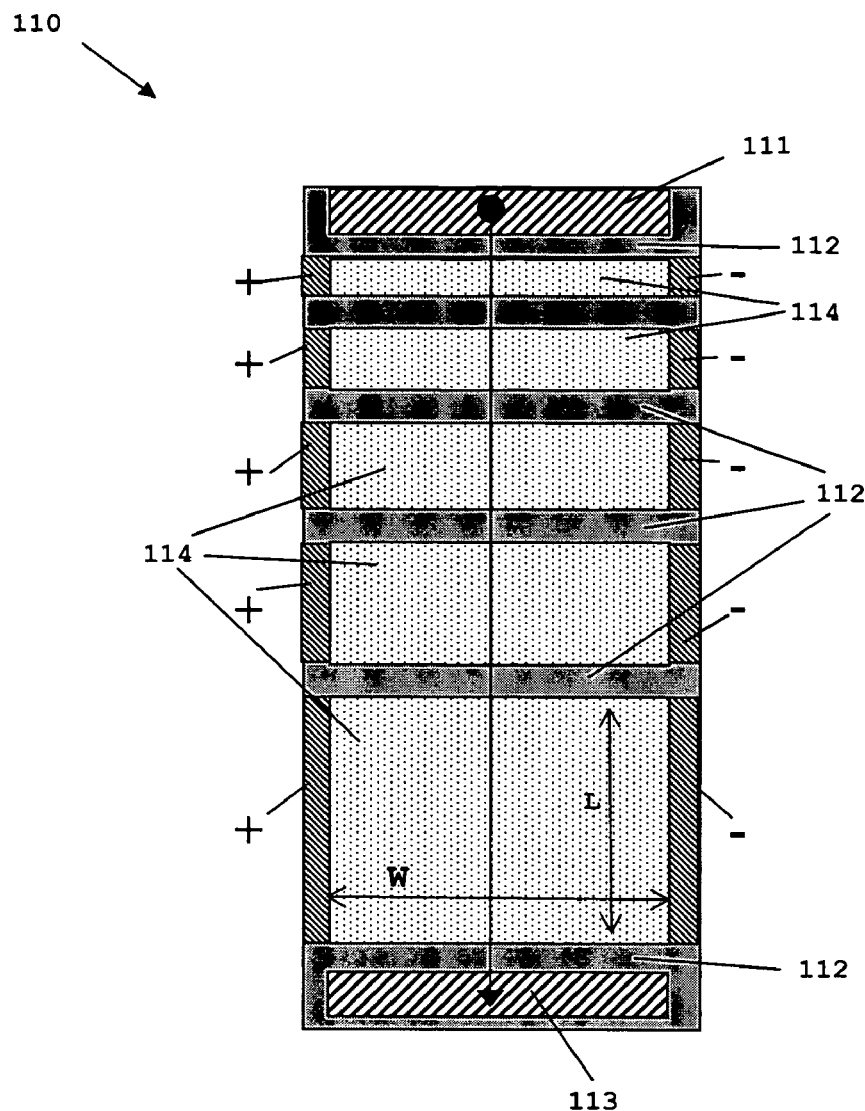
FIG. 3 is a schematic illustration of a second embodiment of a device 110 of the present invention.

Second Geometric Embodiment: FIG. 3 schematically illustrates a second embodiment of a conductimetric assay device 110 of the present invention. In this embodiment, a capture zone has a series of two or more separate tracks 114 arranged in series, and having uncoated plate sections 112 between each track 114. Each track 114 has the same width W, but each track 114 has a different length L along which the fluid sample flows (see arrow). The sample flows from an origin in an absorbent sample pad 111, across each of the tracks 114 of the capture zone 14 successively, to a second absorbent pad 13. Each successive track 114 along the direction of flow (arrow) of the fluid sample has a greater length L than the previous tracks 114. A set of two electrodes (+,−) for each track 114, include an anode (−) and a cathode (+) that are spaced at a distance across the width W of each of the tracks 114. The set of two electrodes (+,−) for each track 114 is linked to an independent circuit (not shown). A first capture agent capable of binding the analyte in affixed to a substrate on each of the separate tracks 114 and a second capture agent with a conductive moiety also capable of binding to the analyte is mixed in the sample fluid. The second capture agent binds to the analyte thereby holding a complex of the analyte and the first capture agent with the conductive moiety between the two electrodes (+,−) to complete the independent circuit and produce a conductive signal.

The capture zone has multiple tracks 114 arranged in a series conformation, each track 114 being progressively longer in length L along the direction of fluid sample flow (arrow). Since each of the tracks 114 is linked to an independent circuit, as each track 114 is saturated with the conductive moiety, its circuit is closed independently. The conductive moiety increases the conductivity of the circuit so as to produce the positive signal. The tracks 114 having shorter lengths L produce positive conductive signals when the sample has low levels of analyte, whereas the tracks 114 with longer lengths L will prevent the sensor from being overloaded with high concentrations of the analyte. The concentration of the analyte can be determined in a roughly quantitative fashion by counting the number of tracks 114 that form closed circuits.

Figure 4:
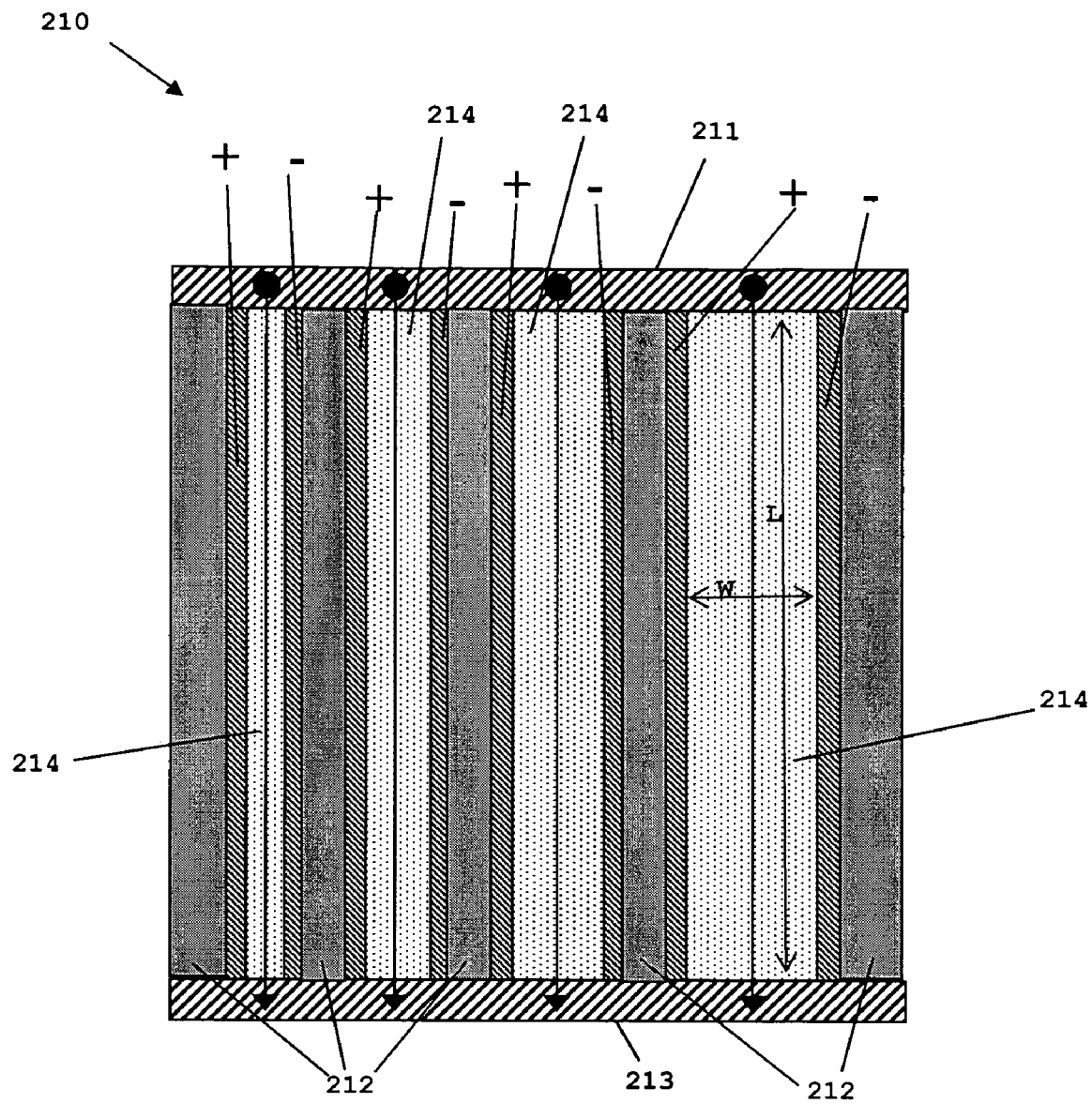
FIG. 4 is a schematic illustration of a third embodiment of a device 210 of the present invention.

Third Geometric Embodiment: FIG. 4 schematically illustrates a third embodiment of a conductimetric assay device 210 of the present invention. In this embodiment, a capture zone is comprised of separate tracks 214 that are arranged in a parallel conformation separated by uncoated plate sections 212. Each of the tracks 214 have a different width W, and each of the tracks 214 has a length L along which a portion of the fluid sample flows. The sample flows from an origin in an absorbent sample pad 211, across each of the tracks 214 of the capture zone 14 simultaneously, to a second absorbent pad 213. Two independent electrodes (+,−) for each track 214 are spaced at a distance across the width W of each of the separate tracks 214 and linked to an independent circuit (not shown). Thus, the distance between the set of two electrodes (+,−) is different for each track 214. A first capture agent capable of binding the analyte is affixed to each of the separate tracks 214. A second capture agent with a conductive moiety capable of binding to the analyte is mixed in the fluid sample. The second capture agent binds to the analyte thereby holding a complex of the analyte and the first capture agent with the conductive moiety between the two electrodes (+,−) of each track 214 to complete the independent circuit (not shown) producing a conductive signal.

In this embodiment, the capture zone consists of multiple tracks 214, each track 214 having an identical length L. Each track 214 has a different width W than the others, as measured perpendicularly to the direction of the solution travel (arrow). Since, each track 214 is linked to an independent circuit (not shown), as each track 214 is saturated it closes its independent circuit, so as to provide a signal. The narrower tracks 214 will give a positive signal with low levels of analyte, whereas the wider tracks 214 will prevent the device 200 from being overloaded with high concentrations of analyte. The concentration of the analyte can be determined in a limited quantitative fashion by counting the number of tracks 214 that form closed circuits.

Figure 5:
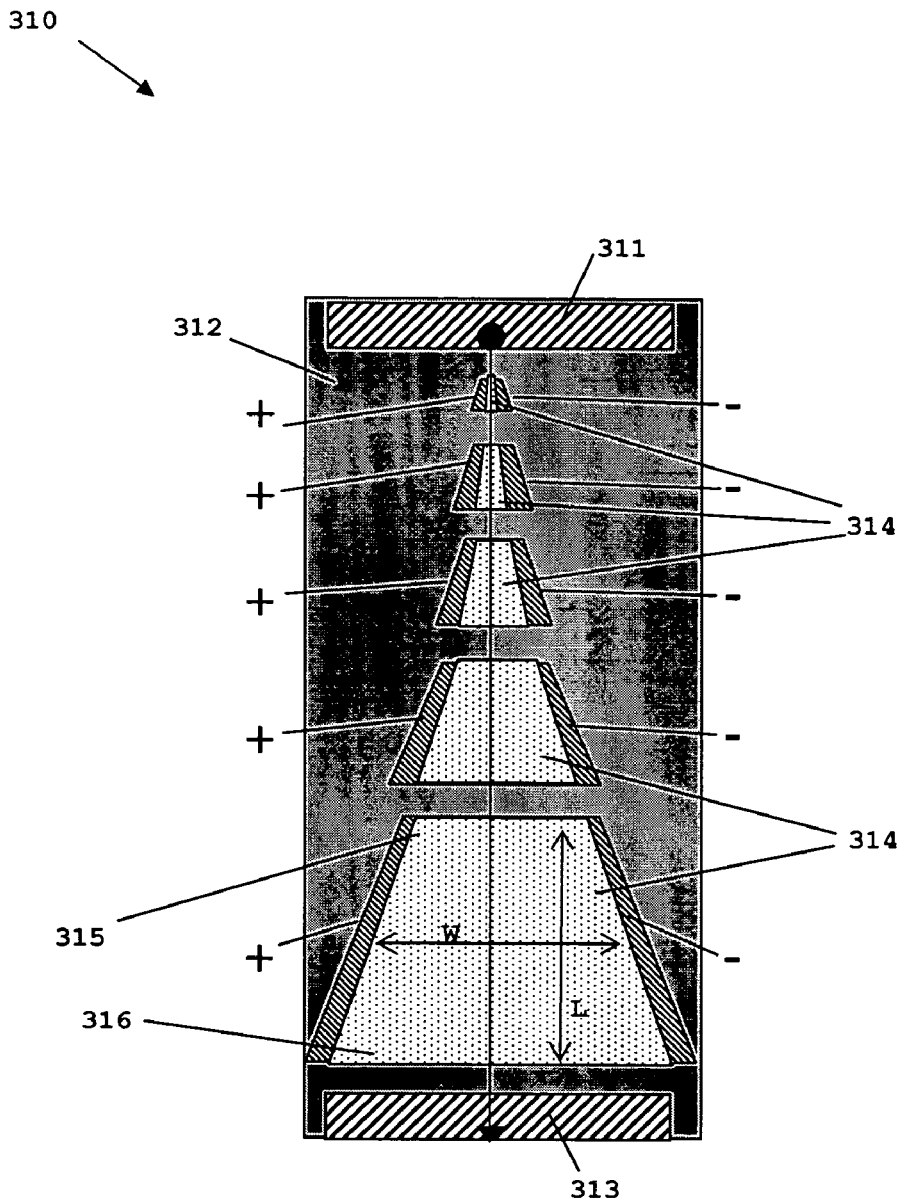
FIG. 5 is a schematic illustration of a fourth embodiment of a device 310 of the present invention.
Figure 6:
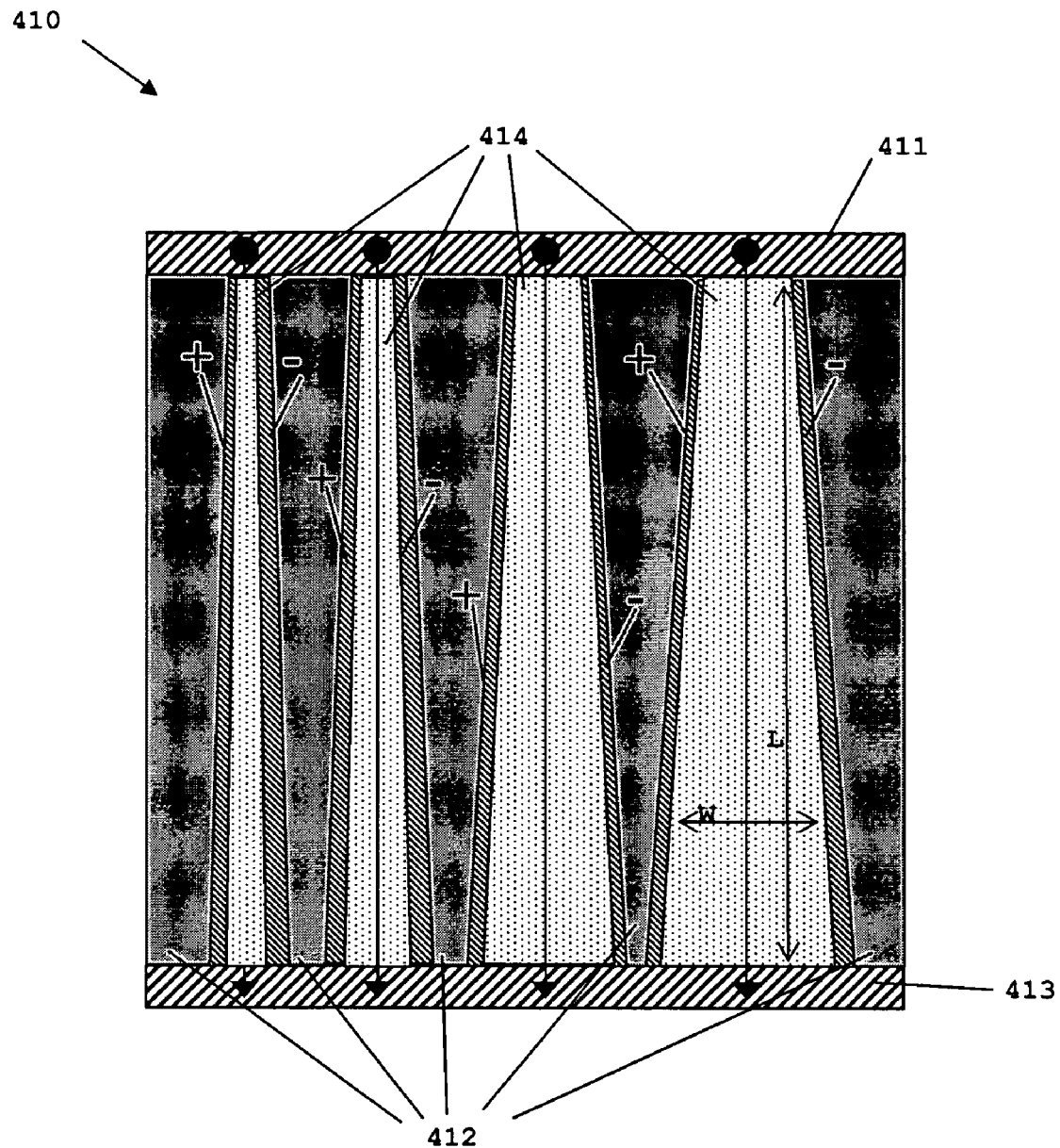
FIG. 6 is a schematic illustration of a fifth embodiment of a device 410 of the present invention.
Figure 6:
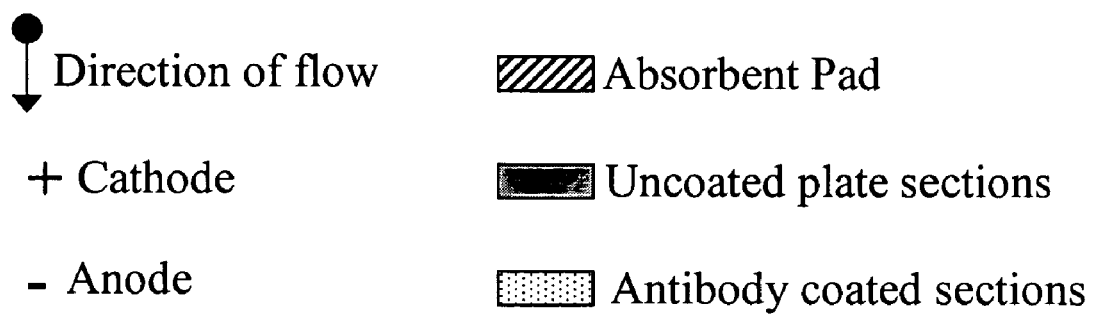

Fourth Geometric Embodiment: In further embodiments, the geometry of the first embodiment can be combined with the second or third embodiments to provide a mixed geometric embodiment. One example of a mixed geometric embodiment of a conductimetric assay device 310 of the present invention is schematically illustrated in FIG. 5. In this embodiment, the geometry of the first embodiment of the device 10 is combined with the series conformation of the second embodiment of the device 110. A capture zone is provided as a series of two or more separate tracks 314 arranged in series and separated by uncoated plate sections 312, each track 314 having a length L along which the fluid sample flows. Each track 114 has an increasing width W from a narrow portion 315 to a wide portion 316 (see largest track). Each of the successive tracks 314 along the direction of flow (arrow) of the fluid sample has a greater length L than the previous tracks 314. The sample flows from an origin in an absorbent sample pad 311, across each of the tracks 314 of the capture zone successively, to a second absorbent pad 313.

A set of two electrodes (+,−), including an anode (−) and a cathode (+), for each track 314 are spaced at a distance across the width W of each of the separate tracks 314. The set of two electrodes (+,−) for each track 114 are each linked to independent circuits (not shown). The width W of each of the tracks 314 increases along the direction of flow (arrow) of the fluid sample such that the distance between the two electrodes (+,−) increases along the direction of flow (arrow). A first capture agent capable of binding the analyte is affixed to a substrate on each of the separate tracks 314. A second capture agent with a conductive moiety capable of binding to the analyte is mixed in the fluid sample. The second capture agent with a conductive moiety binds to the analyte to form a complex that is then bound by the first capture agent affixed between the two electrodes (+,−). This completes the independent circuit to provide a conductive signal. The tracks 314 having shorter lengths L produce positive conductive signals when the sample has low levels of analyte, whereas the tracks 314 with longer lengths L will prevent the device 310 from being overloaded with high concentrations of the analyte. The concentration of the analyte can be determined in a roughly quantitative fashion by counting the number of tracks 314 that form closed circuits.

Fifth Geometric Embodiment: Another example of a mixed geometric embodiment of a conductimetric assay device 410 of the present invention in schematically illustrated in FIG. 6. In this embodiment, the geometry of the first embodiment of the device 10 is combined with the parallel conformation of the third embodiment of the device 310. A capture zone is provided as separate tracks 414 arranged in a parallel conformation, each track having a different varying width W. The sample flows from an origin in an absorbent sample pad 411, across each of the tracks 414 of the capture zone simultaneously, to a second absorbent pad 413. Two independent electrodes (+,−) for each track 414 are spaced at a distance across the varying width W of each of the separate tracks 414 and linked to an independent circuit (not shown).

The width W of each of the two or more separate tracks 414 increases along the direction of flow (arrow) of the fluid sample such that the distance between a set of two electrodes (+,−) for each track 414 increases along the direction of flow (arrow). Each of the tracks 414 has an equal length L along which a portion of the fluid sample flows, while the varying width W of each of the separate tracks 414 is different for each track 414. A first capture agent capable of binding the analyte is affixed to a substrate on each of the separate tracks 414. A second capture agent with a conductive moiety that is capable of binding to the analyte is mixed in the sample fluid. The second capture agent binds to the analyte to form a complex. The first capture agent binds the complex and holds the complex between the two electrodes (+,−). Since the second capture agent with the conductive moiety is held between the electrodes (+,−) it completes the independent circuit of the track 414 to produce a positive conductive signal. The narrower tracks 414 will give a positive signal with low levels of analyte, whereas the wider tracks 414 will prevent the device 410 from being overloaded with high concentrations of analyte. The concentration of the analyte can be determined in a limited quantitative fashion by counting the number of tracks 414 that form closed circuits.

Preventing Analyte Saturation. Another challenge for rapid biosensors, particularly in assays where there is no washing step, is unexpectedly high concentration of analyte. In the scenario where the analyte has only a few epitopes, such as for a protein, when the concentration of the analyte is stoichiometrically higher than the binding agent, (e.g. antibody), some of the analyte will remain completely unbound. This unbound analyte is then present in the solution when it is presented to the first capture agent in the capture zone. The unbound analyte then acts as a competitive inhibitor, binding directly to the first capture agent and thereby blocking the binding of the analyte/binding agent complex. The unbound analyte thereby results in detection of an artificially low signal. Simply increasing the amount of binding agent can help to alleviate this situation. However, if the analyte concentration is low, increasing the amount of binding agent also increases the background signal, resulting in poor performance.

Figure 7A:
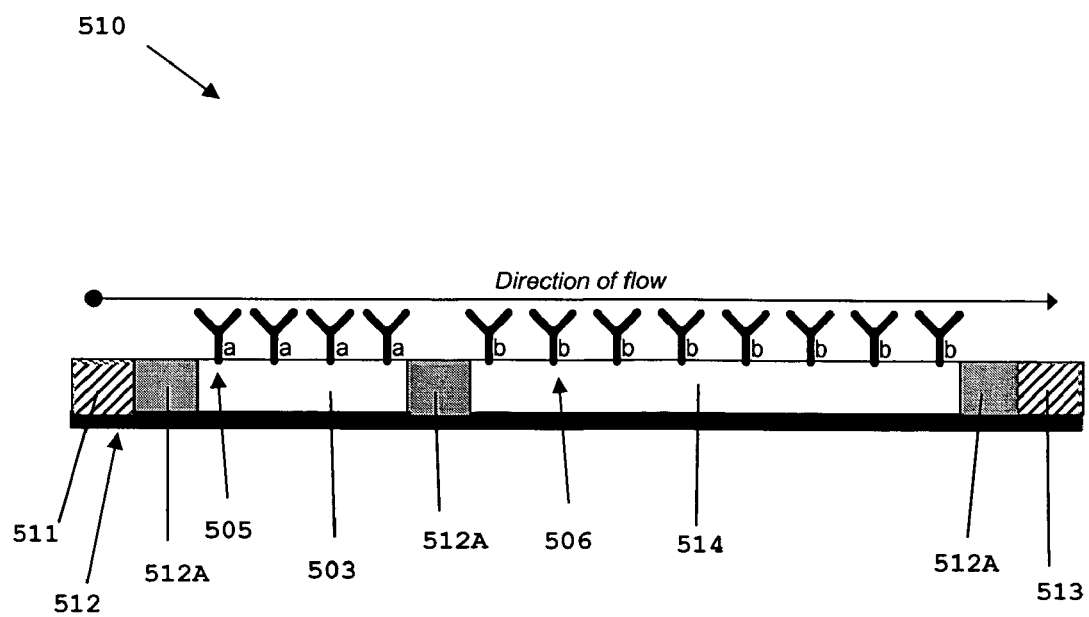
FIGS. 7A and 7B are a schematic cross-sectional views of one embodiment a lateral flow device 510.
Figure 7B:
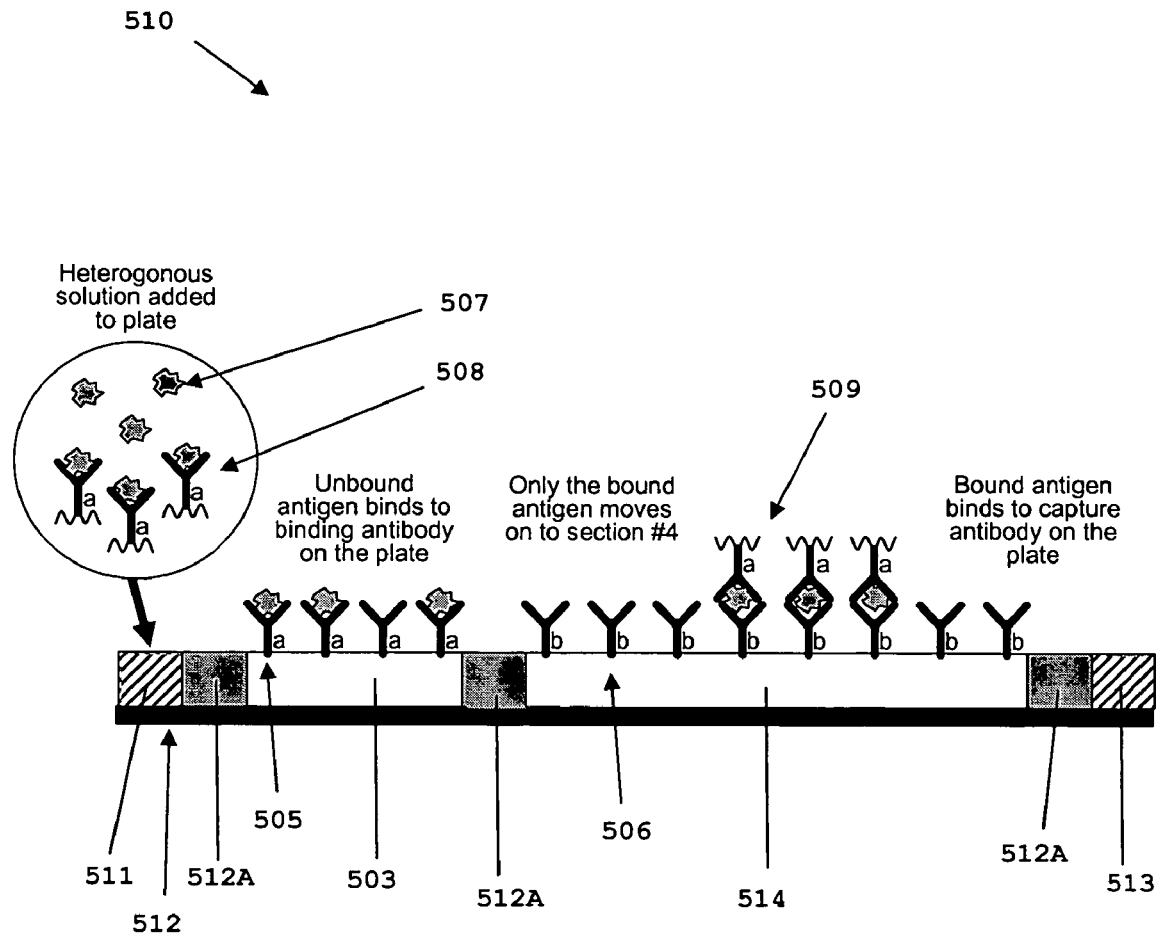
Figure 7B:
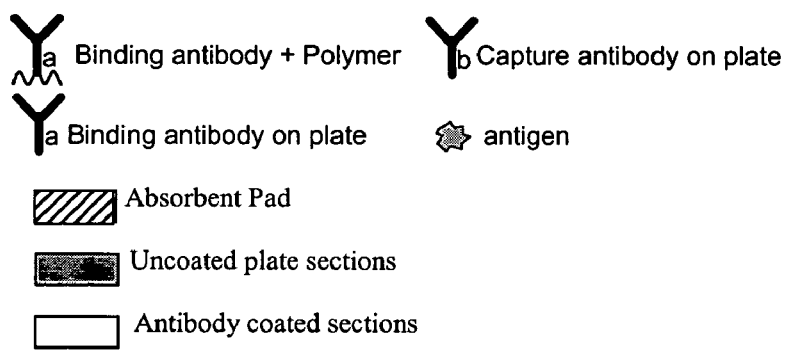

If however, the solution passes first through a pre-capture zone 503 that has a third capture agent, for example a binding antibody ($Y_a$) coating the plate, any remaining free analyte can be removed before reaching the capture zone 514. This fifth embodiment of the device 510, as schematically illustrated in FIGS. 7A and 7B, is used whenever the third capture agent recognizes a region (e.g. an epitope of an antigen 507) of the analyte that is different from the region recognized by the first capture agent, such as a capture antibody ($Y_b$). As illustrated in FIG. 7B, the binding antibody ($Y_a$) or other third capture agent recognizes a region of the analyte that is different from the region recognized by the capture antibody ($Y_b$).

As in the previous embodiments, the sample flows from an origin in an absorbent sample pad 511, across one or more tracks of the capture zone 514 coated with capture antibody ($Y_b$), to a second absorbent pad 513. However, the arrangement of the pads is for illustration only. In the existing pad assembly design, the pads are not aligned on a single surface. Also, it is to be understood that the binding agent and the antigen can be pre-mixed prior to addition to the plate as shown in FIG. 7B, or mixed on the plate prior to crossing the pre-capture zone 503 that is coated with the binding antibody ($Y_a$). The approach used in this fifth embodiment can also be combined with the devices (10, 110, 210, 310, 410) of the previously described embodiments.

In this embodiment of the conductimetric assay device 510, a fluid sample flows between the two absorbent pads (511, 513) supported on a support plate 512 as a substrate. The direction of flow is shown by the arrow in FIG. 7A. The support plate 512 has antibody coated sections as zones 503 and 514. The antibody coated sections (pre-capture zone 503, capture zone 514) are separated by uncoated portions 512A of the support plate 512. The fluid sample first passes over the pre-capture zone 503 coated with a binding antibody ($Y_a$) 505. In the pre-capture zone 503, as shown in FIG. 7B, the binding antibody ($Y_a$) 505, as a third capture agent, binds any free unbound antigen 507. Therefore, only the antigen 507 bound by the binding antibody ($Y_a$) that is coupled with conductive polymer 508 (as the second capture agent with a conductive moiety) will pass over the uncoated portion 512A of the support plate 512 and into the capture zone 514. In the capture zone 514, the capture antibody ($Y_b$) 506 as the first capture agent binds to the antigen 507 that is bound to the binding antibody ($Y_a$) with the conductive polymer 508 to form a conductive complex 509. The presence of the conductive complex 509 completes a circuit (not shown) to provide a positive conductive signal. It is to be understood that each of the previous embodiments (10, 110, 210, 310, 410) can include one or more pre-capture zones upstream of the capture zone 14 or each of the tracks (114, 214, 314, 414) as described in this embodiment of the device.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A conductimetric assay device for the detection of an analyte in a flowing fluid sample comprising:
   (a) a capture zone having a length along a direction which the fluid sample flows over a substrate and an increasing width;
   (b) a set of two electrodes spaced across the increasing width of the capture zone linked to a circuit such that a distance between the set of two electrodes increases along the direction of flow of the fluid sample;
   (c) a first capture agent capable of binding the analyte, the first capture being affixed to the substrate in the capture zone; and
   (d) an analyte-capture agent complex comprising (i) a second capture agent capable of binding the analyte and having a conductive moiety and (ii) analyte bound to the second capture agent, the analyte-capture agent complex being present in the fluid sample which flows over the substrate in said capture zone;
   wherein the first capture agent binds to the analyte in the analyte-capture agent complex, thereby holding the second capture agent with the conductive moiety between the two electrodes to complete the circuit and produce a conductive signal.

2. The conductimetric assay device of claim 1 further comprising a pre-capture zone upstream of the capture zone having a third capture agent capable of binding analyte that is not bound to the second capture agent, such that after the fluid sample mixes with the second capture agent any remaining free analyte is removed from the flowing fluid sample in the pre-capture zone prior to entering the capture zone.

3. The conductimetric assay device of claim 1, wherein the analyte comprises an antigen.

4. The conductimetric assay device of claim 1, wherein the analyte comprises a chemical or biological material selected from the group consisting of proteins, polysaccharides, DNA, and living cells.

5. The conductimetric assay device of one of claims 1, 3, and 4, wherein: (i) the first capture agent and the second capture agent selectively bind to the analyte, and (ii) the first capture agent comprises a first antibody and the second capture agent comprises a second antibody, which first and second antibodies can be the same or different.

6. The conductimetric assay device of one of claims 1, 3, and 4, wherein: (i) the first capture agent and the second capture agent selectively bind to the analyte, and (ii) the first capture agent and the second capture agent are independently selected from the group consisting of lectins, DNA, enzymes, and proteins.

7. The conductimetric assay device of one of claims 1, 3, and 4, wherein the conductive moiety comprises a conductive polymer selected from the group consisting of substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, and conductive polysaccharides.

8. The conductimetric assay device of claim 7, wherein: (i) the first capture agent and the second capture agent selectively bind to the analyte, and (ii) the first capture agent and the second capture agent are independently selected from the group consisting of antibodies, lectins, DNA, enzymes, and proteins.

9. The conductimetric assay device of claim 1, wherein the substrate comprises a non-conductive material selected from the group consisting of non-conductive membranes, silicon, paper, plastic, and glass.

10. The conductimetric assay device of claim 2, wherein (i) the first capture agent binds to a first region of the analyte, (ii) the second and third capture reagents binds to a second region of the analyte that is different from the first region.

11. A conductimetric assay device for the detection of an analyte in a flowing fluid sample comprising:
   (a) a capture zone having a length along a direction which the fluid sample flows over a substrate and an increasing width;
   (b) a set of two electrodes spaced across the increasing width of the capture zone linked to a circuit such that a distance between the set of two electrodes increases along the direction of flow of the fluid sample; and
   (c) a first capture agent capable of binding the analyte, the first capture being affixed to the substrate in the capture zone.

12. The conductimetric assay device of claim 11, wherein: (i) the first capture agent selectively binds to the analyte, and (ii) the first capture agent is selected from the group consisting of antibodies, lectins, DNA, enzymes, and proteins.

13. The conductimetric assay device of claim 12, wherein the analyte comprises a chemical or biological material selected from the group consisting of proteins, polysaccharides, DNA, and living cells.

14. The conductimetric assay device of claim 11, wherein the substrate comprises a non-conductive material selected from the group consisting of non-conductive membranes, silicon, paper, plastic, and glass.

15. The conductimetric assay device of claim 11 further comprising a pre-capture zone upstream of the capture zone having a third capture agent capable of binding analyte, wherein the first and third capture agents bind to different regions of the analyte.

* * * * *